(12) United States Patent
Chan et al.

(10) Patent No.: US 7,674,900 B2
(45) Date of Patent: Mar. 9, 2010

(54) CHIRAL TERTIARY AMINOALKYLNAPHTHOLS

(75) Inventors: Albert Sun-Chi Chan, Hung Hom (HK); Gang Chen, Chengdu (CN); Rongwei Guo, Mississauga (CA); Jing Wu, Zhejiang (CN)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 0 days.

(21) Appl. No.: 11/578,708

(22) PCT Filed: May 11, 2005

(86) PCT No.: PCT/CN2005/000654

§ 371 (c)(1),
(2), (4) Date: Jan. 26, 2007

(87) PCT Pub. No.: WO2005/108377

PCT Pub. Date: Nov. 17, 2005

(65) Prior Publication Data

US 2007/0225497 A1   Sep. 27, 2007

Related U.S. Application Data

(60) Provisional application No. 60/569,826, filed on May 11, 2004.

(51) Int. Cl.
*C07F 9/6544* (2006.01)
(52) U.S. Cl. .................................................... 544/243
(58) Field of Classification Search .................. 544/243
See application file for complete search history.

(56) References Cited

U.S. PATENT DOCUMENTS

| 4,739,084 | A | 4/1988 | Takaya et al. ................. 556/21 |
| 5,872,273 | A | 2/1999 | Saito et al. .................... 556/21 |

OTHER PUBLICATIONS

Japanese Abstract, Yamamoto. JP 2000044544, Feb. 15, 2000 Dihalo-bipyrimidine compound(s) suitable for use in electrochromic materials—useful as ligand in formation of rigid, symmetrical coordinate complex and can be polymerized in presence of reduced metal.
Bookham et al., "Stereoselective addition reactions of diphenylphosphine to pyridyl and pyrimidylalkynes: chiral 1,2-diheteroaryl-1,2-bis(diphenylphosphino)ethanes and their Group 6 metal carbonyl complexes", Journal of Organometallic Chemistry 577, pp. 305-315 (1999).
Bookham et al., "Dynamic coordinative exchange in rhodium (1) complexes of chiral diphosphines bearing pendant pyridyl donor groups". J. Chem. Soc. Dalton Trans., pp. 975-980, (2000).
Cosgrave et al., Preoperative atrial histological changes are not associated with postoperative atrial fibrillation, Cardiovascular Pathology 15, pp. 213-217 (2006).
Kabir et all, "Reactivity of [μ-H)Os$_3$(CO)$_8${Ph$_2$PCH$_2$P(Ph)C$_6$H$_4$}] with organic heterothiols; X-ray structures of [H(μ H)Os$_3$(CO$_8$ ($^2$-pyS) {Ph$_2$PCH$_2$P(Ph)C$_6$H$_4$}] and [Os$_3$ (CO)$_8$ (μ- $^2$pyS){Ph$_2$PCH$_2$(Ph)C$_6$H$_4$}]"Journal of Organometallic Chemistry 616, pp. 157-164 (2000).
Barry M. Trost, et al: "Asymmetric Transition Metal-Catalyzed Allylic Alkylations", Chemical Rev., vol. 96, 1996, pp. 395-422.
Zimmermann, Helmuth et al: "Structure of 5-(diphenylphosphino)uracil", Acta Crystallographica, Section C: Crystal Structure Communications, (1987), C43, 1798-1800.

*Primary Examiner*—James O Wilson
*Assistant Examiner*—Cecilia M Jaisle
(74) *Attorney, Agent, or Firm*—Sandra S. Shim

(57) ABSTRACT

The present invention provides bipyrimidinyl diphosphine compounds of the formula

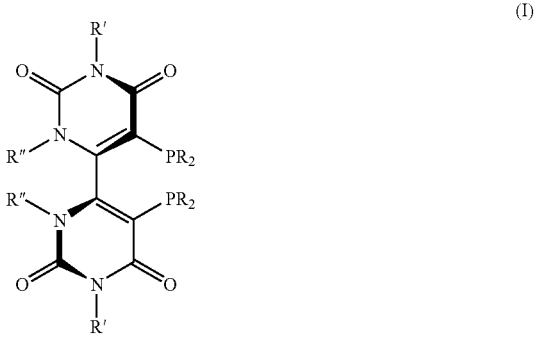

(I)

wherein
R is optionally substituted alkyl, cycloalkyl, aryl or heteroaryl;
R' and R" are independently optionally substituted alkyl, cycloalkyl, aryl or heteroaryl;
or an enantiomer thereof; or an enantiomeric mixture thereof.

The compounds of the formula (I) are chiral atropisomeric bipyrimidinyl diphosphine compounds and, thus, may be employed as ligands to generate chiral transition metal catalysts which may be applied in a variety of asymmetric reactions, e.g., in palladium catalyzed asymmetric allylic substitution reactions. The compounds of the present invention are easily accessible in high enantiomeric purity according to the methods disclosed herein.

6 Claims, No Drawings

CHIRAL TERTIARY AMINOALKYLNAPHTHOLS

This application claims benefit of U.S. Provisional Application No. 60/569,826, filed May 11, 2004.

The design and synthesis of chiral phosphine ligands have played a significant role in the development of efficient asymmetric transition metal catalyzed reactions. Thus, a large number of efficient chiral diphosphine ligands have been synthesized and evaluated. Chiral atropisomeric diphosphines, such as BINAP (U.S. Pat. No. 4,739,084; *J. Am. Chem. Soc.* 1980, 102, 7932), BIPHEP (*Helv. Chim. Acta.* 1988, 71, 897), MeO-BIPHEP (*Helv. Chim. Acta.* 1991, 74, 370), BICHEP, (U.S. Pat. No. 5,021,593; *Chem. Lett.* 1989, 1849), SEGPHOS (U.S. Pat. No. 5,872,273; *Adv. Synth. Catal.* 2001, 343, 264), SYNPHOS (*Tetrahedron Lett.* 2002, 43, 2789; *Tetrahedron Lett.* 2003, 44, 823), TunaPhos (*J. Org. Chem.* 2000, 65, 6223), tetraMe-BITANP (U.S. Pat. No. 5,907,045; *J. Chem. Soc., Chem. Commun.* 1995, 685), tetraMe-BTIOP (*J. Org. Chem.* 2000, 65, 2043), and P-Phos (U.S. Pat. No. 5,886,182; *J. Am. Chem. Soc.* 2000, 122, 11513), exhibit excellent enantioselectivity particularly in rhodium (Rh), ruthenium (Ru) and palladium (Pd) catalyzed asymmetric reactions. Among these ligands, the P-Phos family embodies a nitrogen-containing biheterocyclic structure, as illustrated below in FIG. 1. The rhodium and ruthenium complexes formed with the P-Phos ligands have been found to catalyze the asymmetric hydrogenation of a wide range of substrates with excellent enantioselectivity.

FIG. 1.

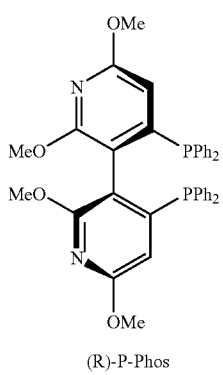

(R)-P-Phos

Despite the extensive research in this area, there are still a variety of reactions in which only modest enantioselectivites has been achieved with these ligands. For example, in palladium catalyzed allylic substitution reactions, which are extremely powerful tools for the controlled introduction of carbon-carbon and carbon-heteroatom bond formation, only a few chiral diphosphine ligands have found an application (*Chem. Rev.*, 1996, 96, 395). Thus, it remains highly desirable to develop novel chiral diphosphine ligands with special properties and which are selective and effective in a variety of asymmetric catalytic reactions such as asymmetric allylic substitution reactions, and which are synthetically easily accessible in high optical purity.

Accordingly, the present invention provides bipyrimidinyl diphosphine compounds of the formula

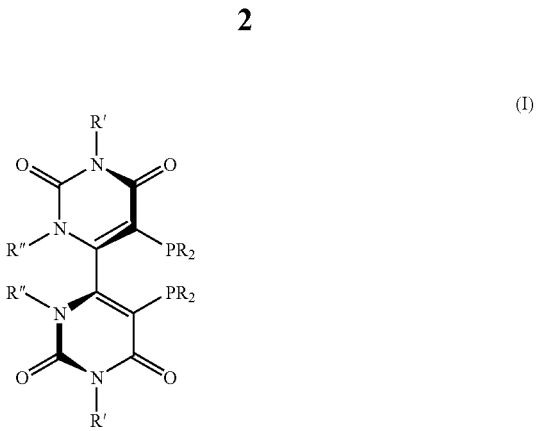

wherein
R is optionally substituted alkyl, cycloalkyl, aryl or heteroaryl;
R' and R" are independently optionally substituted alkyl, cycloalkyl, aryl or heteroaryl;
or an enantiomer thereof; or an enantiomeric mixture thereof.

The compounds of the formula (I) are chiral atropisomeric bipyrimidinyl diphosphine compounds and, thus, may be employed as ligands to generate chiral transition metal catalysts which may be applied in a variety of asymmetric reactions, e.g., in palladium catalyzed asymmetric allylic substitution reactions. The compounds of the present invention are easily accessible in high enantiomeric purity according to the methods disclosed herein.

Other objects, features, advantages and aspects of the present invention will become apparent to those skilled in the art from the following description and appended claims. It should be understood, however, that the following description, appended claims, and specific examples, while indicating preferred embodiments of the invention, are given by way of illustration only. Various changes and modifications within the spirit and scope of the disclosed invention will become readily apparent to those skilled in the art from reading the following.

Listed below are definitions of various terms used to describe the compounds of the present invention. These definitions apply to the terms as they are used throughout the specification unless they are otherwise limited in specific instances either individually or as part of a larger group.

The term "optionally substituted alkyl" refers to unsubstituted or substituted straight- or branched-chain hydrocarbon groups having 1-20 carbon atoms, preferably 1-7 carbon atoms. Exemplary unsubstituted alkyl groups include methyl, ethyl, propyl, isopropyl, n-butyl, t-butyl, isobutyl, pentyl, neopentyl, hexyl, isohexyl, heptyl, octyl and the like. Substituted alkyl groups include, but are not limited to, alkyl groups substituted by one or more of the following groups: hydroxyl, alkylamino, dialkylamino, cycloalkyl, alkenyl or alkoxy.

The term "lower alkyl" refers to those optionally substituted alkyl groups as described above having 1-6 carbon atoms.

The term "alkenyl" refers to any of the above alkyl groups having at least two carbon atoms and further containing a carbon to carbon double bond at the point of attachment. Groups having 2 to 4 carbon atoms are preferred.

The term "halogen", "halide" or "halo" refers to fluorine, chlorine, bromine and iodine.

The term "alkoxy" refers to alkyl-O—.

The term "cycloalkyl" refers to optionally substituted monocyclic aliphatic hydrocarbon groups of 3-6 carbon atoms, which may be substituted by one or more substituents, such as alkyl or alkoxy.

Exemplary monocyclic hydrocarbon groups include, but are not limited to, cyclopropyl, cyclobutyl, cyclopentyl, cyclohexyl and the like.

The term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted alkyl, cycloalkyl or alkoxy.

The term "monocyclic aryl" refers to optionally substituted phenyl as described under aryl.

The term "heteroaryl" refers to an aromatic heterocycle, for example monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like; optionally substituted by, e.g., lower alkyl or lower alkoxy.

As described herein above, the present invention relates to compounds of formula (I), to methods for their preparation, and to use of such compounds in asymmetric catalysis. Compounds of the present invention are particularly useful when employed as chiral ligands in palladium catalyzed asymmetric allylic substitution reactions.

When required, protecting groups may be introduced to protect the functional groups present from undesired reactions with reaction components under the conditions used for carrying out a particular chemical transformation of the present invention. The need and choice of protecting groups for a particular reaction is known to those skilled in the art and depends on the nature of the functional group to be protected (amino, hydroxy etc.), the structure and stability of the molecule of which the substituent is a part and the reaction conditions.

Well-known protecting groups that meet these conditions and their introduction and removal are described, for example, in McOmie, "Protective Groups in Organic Chemistry", Plenum Press, London, N.Y. (1973); Greene and Wuts, "Protective Groups in Organic Synthesis", John Wiley and Sons, Inc., NY (1999).

Preferred are the compounds of formula (I) wherein
R is monocyclic aryl;
R' and R" are independently lower alkyl;

or an enantiomer thereof; or an enantiomeric mixture thereof.

Further preferred are the compounds of formula (I) wherein
R is phenyl;
R' and R" are methyl;

or an enantiomer thereof; or an enantiomeric mixture thereof.

Particular embodiments of the invention are:
(R)-5,5'-bis(disubstitutedphosphino)-1,1',3,3'-tetraalkyl-4,4'-bipyrimidine-2,2',6,6'-(1H,1'H,3H,3'H)-tetrone, also designated as (R)-PM-Phos; and
(S)-5,5'-bis(disubstitutedphosphino)-1,1',3,3'-tetraalkyl-4,4'-bipyrimidine-2,2',6,6'-(1H,1'H,3H,3'H)-tetrone, also designated as (S)-PM-Phos.

The compounds of the present invention preferably have an optical purity of at least 85% enantiomeric excess (ee), more preferably at least 95% ee, and most preferably at least 98% ee.

The compounds of the present invention may be employed to generate a chiral transition metal catalyst comprising a suitable transition metal bound to a compound of the formula

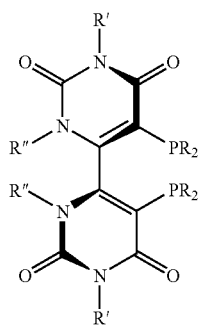

(I)

wherein
R is optionally substituted alkyl, cycloalkyl, aryl or heteroaryl;
R' and R" are independently optionally substituted alkyl, cycloalkyl, aryl or heteroaryl;

or an enantiomer thereof; or an enantiomeric mixture thereof.

Particularly useful are the catalysts of the present invention wherein the transition metal is bound to a compound of formula (I) wherein
R is monocyclic aryl;
R' and R" are independently lower alkyl;

or an enantiomer thereof; or an enantiomeric mixture thereof.

Especially useful are the catalysts of the present invention wherein the transition metal is bound to a compound of formula (I) wherein
R is phenyl;
R' and R" are methyl;

or an enantiomer thereof; or an enantiomeric mixture thereof.

Especially useful are also the catalysts of the present invention wherein the transition metal is bound to a compound of formula (I) which is selected from the group consisting of:
(R)-5,5'-bis(disubstitutedphosphino)-1,1',3,3'-tetraalkyl-4,4'-bipyrimidine-2,2',6,6'-(1H,1'H,3H,3'H)-tetrone; and
(S)-5,5'-bis(disubstitutedphosphino)-1,1',3,3'-tetraalkyl-4,4'-bipyrimidine-2,2',6,6'-(1H,1'H,3H,3'H)-tetrone.

Suitable transition metals for the catalyst system of the present invention include, but are not limited to, copper (Cu), iridium (Ir), nickel (Ni), palladium (Pd), platinum (Pt), rhodium (Rh) and ruthenium (Ru). Preferably, the transition metal is palladium.

Particularly useful are the catalysts of the present invention wherein the transition metal is palladium, and the transition metal is bound to a compound of formula (I) wherein
R is monocyclic aryl;
R' and R" are independently lower alkyl;

or an enantiomer thereof; or an enantiomeric mixture thereof.

Especially useful are the catalysts of the present invention wherein the transition metal is palladium, and the transition metal is bound to a compound of formula (I) wherein
R is phenyl;
R' and R" are methyl;

or an enantiomer thereof; or an enantiomeric mixture thereof.

Especially useful are also the catalysts of the present invention wherein the transition metal is palladium, and the transition metal is bound to a compound of formula (I) which is selected from the group consisting of:
(R)-5,5'-bis(disubstitutedphosphino)-1,1',3,3'-tetraalkyl-4,4'-bipyrimidine-2,2',6,6'-(1H,1'H,3H,3'H)-tetrone; and
(S)-5,5'-bis(disubstitutedphosphino)-1,1',3,3'-tetraalkyl-4,4'-bipyrimidine-2,2',6,6'-(1H,1'H,3H,3'H)-tetrone.

The compounds of the present invention may be prepared by deprotonating a compound of the formula

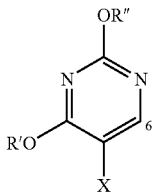

(II)

wherein R' and R" have meanings as defined herein above and X represents halogen, such as iodide, bromide or chloride, with a base such as lithium diisopropylamide (LDA) or lithium bis(trimethylsilyl)amide in an inert solvent such as tetrahydrofuran (THF), preferably, at a temperature of about −78° C. The resulting anion, wherein X has migrated spontaneously to the 6-position, may then be treated with a compound of the formula

 (III)

wherein R has a meaning as defined herein above, to afford a compound of the formula

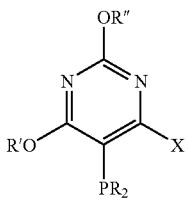

(IV)

wherein R, R', R" and X have meanings as defined herein above. Compounds of formulae (II) and (III) are known, or if they are novel, they may be prepared according to methods well known in the art.

A resulting compound of formula (IV) may then be treated with an oxidizing agent such as hydrogen peroxide in an inert solvent such as acetone to afford a compound of the formula

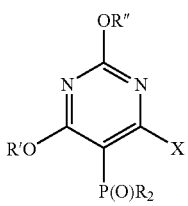

(V)

wherein R, R', R" and X have meanings as defined herein above. Preferably, the oxidation is carried out at a temperature ranging from about −10° C. to about 0° C.

A resulting compound of formula (V) may be converted to a compound of formula (VI) under conditions of Ullmann coupling, e.g., a compound of formula (V) may be treated with copper powder in an inert solvent, such as N,N-dimethylformamide (DMF) or dimethylsulfoxide (DMSO), to afford a compound of the formula

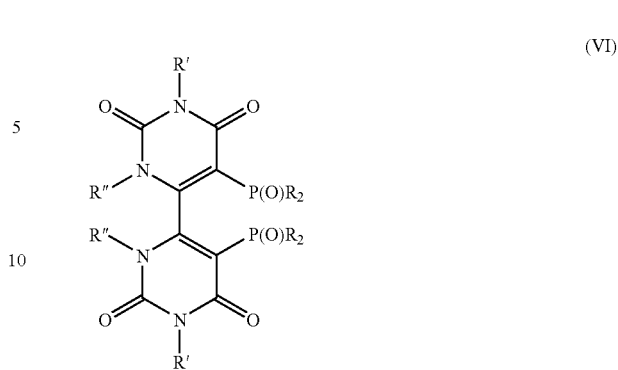

(VI)

wherein R, R' and R" have meanings as defined herein above. The Ullmann coupling reaction is preferably conducted at a temperature ranging from about 100° C. to about 160° C., preferably at a temperature of about 140° C., in the presence of an inorganic salt such as sodium carbonate, potassium carbonate or sodium oxalate, or a mixture of salts thereof, to facilitate the coupling reaction. Interestingly, the coupling reaction is accompanied by the spontaneous migration of the R' and R" groups from the oxygen atoms to the nitrogen atoms.

A resulting racemic compound of formula (VI) may then be resolved into its optical antipodes, i.e., enantiomers, by known methods, e.g., by separation of the diastereoisomeric salts thereof, e.g., by fractional crystallization of a (+)- or (−)-dibenzoyltartaric acid salt thereof, e.g., from a 1:1-mixture of ethyl acetate and chloroform. The optically active compound of the formula

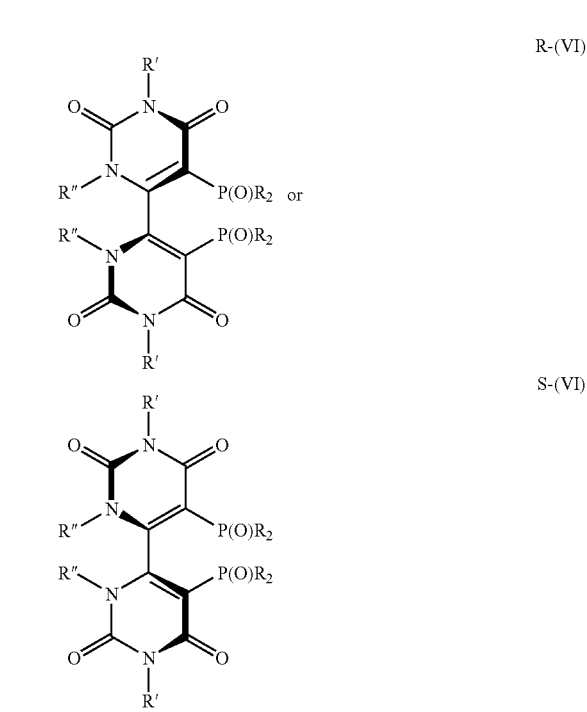

R-(VI)

or

S-(VI)

wherein R, R' and R" have meanings as defined herein above, may then be liberated, e.g., by treatment with base such as aqueous sodium hydroxide (NaOH) to afford a free compound of formula R-(VI) or S-(VI), or an enantiomeric mixture thereof. A racemic compound of formula (VI) may also be resolved by chiral chromatography, e.g., high pressure liquid chromatography (HPLC) using a chiral adsorbent.

Finally, a compound of formula (VI), or an enantiomer thereof, or an enantiomeric mixture thereof, may be treated with a reducing agent, such as trichlorosilane, in the presence of an organic base, such as triethylamine or tri-n-butylamine, and an aromatic hydrocarbon solvent, such as toluene or xylene, to afford a compound of formula (I), or an enantiomer thereof, or an enantiomeric mixture thereof, respectively, wherein R, R' and R" have meanings as defined herein above. Preferably, the reduction is conducted in toluene in an autoclave, at a temperature of about 120° C.

The compounds of formula (I) may then be converted to chiral transition metal catalysts of the present invention by reacting a compound of formula (I), or an enantiomer thereof, or an enantiomeric mixture thereof, with a suitable transition metal salt, or a complex thereof, to afford a catalyst of the present invention. The choice of a suitable transition metal salt, or a complex thereof, is generally known to those skilled in the art and depends on the nature of the asymmetric reaction to be performed. A suitable transition metal salt, or a complex thereof, for the preparation of a catalyst of the present invention may be selected, e.g., from those described herein in the illustrative examples. Further examples of such transition metal salts may be found, e.g., in Seyden-Penne, "*Chiral Auxiliaries and Ligands in Asymmetric Synthesis*", John Wiley & Sons, Inc., NY (1995). A catalyst of the present invention may be generated in situ, or it may be isolated prior to use.

The catalysts of the present invention obtainable as described herein may be employed for converting a racemic or a prochiral substrate to a chiral product under reaction conditions otherwise suitable for asymmetric induction.

Such asymmetric reactions include, but are not limited to, catalytic hydrogenation, hydrosilylation, hydroboration, hydroformylation, hydrocarboxylation, hydroacylation, Heck reaction and allylic substitution reactions. The catalysts of the present invention are especially effective when employed in allylic substitution reactions. For example, a compound of formula (I) may be reacted with a palladium complex such as a dimer of allyl palladium chloride or tris(dibenzylideneacetone)palladium in a suitable organic solvent such as dichloromethane (DCM) to obtain a catalyst of the present invention. The resulting catalyst may then be used in situ in a suitable palladium catalyzed reaction, e.g., in an asymmetric allylic substitution reaction such as an allylic alkylation or allylic amination reaction.

As illustrated in Tables 1 and 2, the catalyst system of the present invention may be employed effectively in asymmetric palladium catalyzed allylic alkylation and amination reactions with good catalytic activity and enantioselectivity.

The results of a palladium catalyzed allylic alkylation using a trimethylsilyl enolate of dimethylmalonate as the nucleophile and (R)-PM-Phos as the chiral ligand under various reactions conditions are summarized in Table 1. As expected, better enantioselectivities are obtained at lower reaction temperatures at the expense of the reaction rate. Interestingly, the best enantioselectivity in each case is achieved when the enolate is generated using sodium aceate (NaOAc) as the base.

TABLE 1

Palladium catalyzed allylic alkylation with (R)-PM-Phos.

| Entry | Base | Pd/substrate | T/° C. | t/h | % Conversion[b] | % ee (S)[a] |
|---|---|---|---|---|---|---|
| 1 | LiOAc | 1/100 | 25 | 1.5 | 99 | 82.6 |
| 2 | NaOAc | 1/100 | 25 | 2 | 99 | 85 |
| 3 | KOAc | 1/100 | 25 | 1.5 | 99 | 82 |
| 4 | $Cs_2CO_3$ | 1/100 | 25 | 1.5 | 99 | 81 |
| 5 | LiOAc | 1/100 | 0 | 3 | 99 | 86 |
| 6 | NaOAc | 1/100 | 0 | 6 | 99 | 88.5 |
| 7 | KOAc | 1/100 | 0 | 10 | 95 | 86.5 |
| 8 | $Cs_2CO_3$ | 1/100 | 0 | 10 | 99 | 87 |
| 9 | NaOAc | 1/50 | −20 | 12 | 99 | 92 |
| 10 | NaOAc | 1/50 | −40 | 24 | 91 | 95 |

[a]The enantiomeric excess is determined by HPLC (Daicel Chiracel AD column, 1.0 mL/min, hexane:i-PrOH - 95:5).
[b]The conversion of the substrate is determined by $^1$H NMR spectroscopy.
[c]N,O-Bis(trimethylsilyl)acetamide.

Similarly, the results of a palladium catalyzed allylic amination using benzylamine as the nucleophile and (R)-PM-Phos as the chiral ligand are summarized in Table 2. As exemplified in entries 1 and 2, an asymmetric allylic amination employing a catalyst of the present invention provides chiral allylic amines with considerably higher catalytic activity and enantioselectivity than that obtained with the well known diphosphine ligand BINAP under identical reaction conditions.

TABLE 2

Palladium catalyzed allylic amination with (R)-PM-Phos and (S)-BINAP.

| Entry | Ligand | Solvent | Pd/substrate | T/° C. | t/h | % Conversion[b] | % ee[a] |
|---|---|---|---|---|---|---|---|
| 1 | (S)-Binap | DCM | 1/50 | 25 | 24 | 67 | 28 (S) |
| 2 | (R)-PM-Phos | DCM | 1/50 | 25 | 2 | 99 | 81 (R) |
| 3 | (R)-PM-Phos | DCM | 1/50 | 0 | 24 | 96 | 88 (R) |
| 4 | (R)-PM-Phos | $CH_3CN$ | 1/50 | −20 | 15 | 99 | 94.7 (R) |

[a]The enantiomeric excess is determined by HPLC (Daicel Chiracel OJ column, 0.6 mL/min, hexane:i-PrOH - 90:10).
[b]The conversion of the substrate is determined by $^1$H NMR spectroscopy.

The following Examples are intended to further illustrate the invention and are not to be construed as being limitations thereon. If not mentioned otherwise, all evaporations are performed under reduced pressure, preferably between about 5 and 50 mmHg. The structure of final products, intermediates and starting materials is confirmed by standard analytical methods, e.g., microanalysis, melting point, and spectroscopic characteristics, e.g., MS, IR, NMR. Abbreviations used are those conventional in the art.

EXAMPLE 1

4-Bromo-5-(diphenylphosphino)-2,6-dimethoxypyrimidine

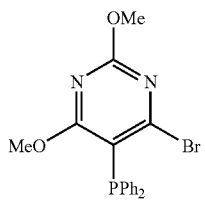

To a magnetically stirred solution of 8.2 mL (58.4 mmol) of diisopropylamine in 50 mL of dried THF at 0° C. is dropwisely added 34.2 mL (54.7 mmol) of a solution of n-BuLi (1.6 M) in hexane. After the addition, the resulting solution is maintained at room temperature for 1 h, then cooled down to −78° C. To the above LDA solution, a solution of 5-bromo-2,4-dimethoxypyrimidine (10 g, 45.6 mmol) in 50 mL of THF is dropwisely added in 1 h. The temperature is allowed o rise a little until the color of the solution became dark brown, and then cooled down to −78° C. again. A solution of ClPPh$_2$ (10 mL, 55.5 mmol) in 50 mL of THF is dropwisely added to the above solution. And finally the temperature is allowed to naturally rise to room temperature. The reaction mixture is stirred at ambient temperature for additional 12 h. At the end, the reaction mixture is poured into 300 mL of water with vigorous stirring. The product is extracted with DCM (3×50 mL). The combined extract is washed with water for 3 times and dried with anhydrous sodium sulfate. The solvent is removed off in vacuo to give a crude product which is purified by flash chromatography with DCM as eluant and then by recrystallization in a 1:1 mixture of methanol and acetone to give pure, white powdery 4-bromo-5-(diphenylphosphino)-2,6-dimethoxypyrimidine: $^1$H NMR (500 MHz) (CDCl$_3$) δ 3.55 (s, 3H, OCH$_3$), 4.02 (s, 3H, OCH$_3$), 7.31-7.38 (m, 10H, PhH); $^{13}$C-NMR (126 MHz) (CDCl$_3$) δ 54.4, 55.8, 110.9 (d, J=24.0 Hz), 128.4 (d, J=5.7 Hz), 128.6, 132.6 (d, J=20.1 Hz), 135.3 (d, J=10.6 Hz), 162.6 (d, J=41.5 Hz), 165.0, 172.3 (d, J=2.9 Hz); $^{31}$P-NMR (202 MHz) (CDCl$_3$) δ −9.0 (s).

EXAMPLE 2

4-Bromo-5-(diphenylphosphinoyl)-2,6-dimethoxypyrimidine

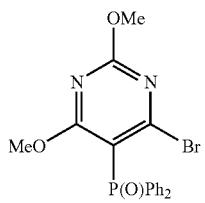

A round bottom flask with a magnetic stirrer is charged with 4-bromo-5-(diphenylphosphino)-2,6-dimethoxypyrimidine from Example 1 (13 g) and 150 mL of acetone, the reaction mixture is stirred vigorously and cooled down to 0° C. To this mixture is slowly added 15 mL of ca. 35% hydrogen peroxide. The reaction is monitored by TLC. After the solid is completely dissolved, the reaction is completed. After adding 100 mL of water, the product is extracted with DCM (3×50 mL). The combined extract is washed with water for three times and dried with anhydrous sodium sulfate. The solution is concentrated in vacuo to give a crude product which is purified by recrystallization from a 1:1 mixture of ethyl acetate and hexane to afford pure, colorless crystalline 4-bromo-5-(diphenylphosphinoyl)-2,6-dimethoxypyrimidine: $^1$H NMR (500 MHz) (CDCl$_3$) δ 3.49 (s, 3H), 4.02 (s, 3H), 7.43-7.46 (m, 4H), 7.50-7.54 (m, 2H), 7.67-7.72 (m, 4H); $^{13}$C-NMR (126 MHz) (CDCl$_3$) δ 54.7, 56.1, 128.6 (d, J=12.6 Hz), 131.5 (d, J=10.6 Hz), 132.0, 133.1, 134.0, 158.8 (d, J=6.8 Hz), 165.2, 172.3 (d, J=5.8 Hz); $^{31}$P-NMR (202 MHz) (CDCl$_3$) δ 24.8 (s).

EXAMPLE 3

5,5'-Bis(diphenylphosphinoyl)-1,1',3,3'-tetramethyl-4,4'-bipyrimidine-2,2',6,6'-(1H,1'H,3H,3'H)-tetrone

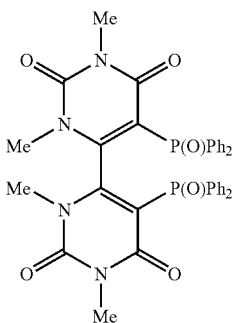

A mixture of 4-bromo-5-(diphenylphosphinoyl)-2,6-dimethoxypyrimidine from Example 2 (4.8 g, 11.5 mmol), copper powder (7.36 g, 115 mmol), sodium carbonate (6.1 g, 58 mmol) and 10 mL of dried DMF is stirred at 140° C. for 24 h under nitrogen atmosphere. The mixture is evaporated to almost dryness. The residue is boiled for a few minutes with 50 mL of chloroform, the insoluble solid is removed by filtration and is washed with hot chloroform (2×10 mL). The combined filtrate is washed with 5 N aqueous ammonia (2×100 mL), water (2×100 mL) and brine (100 mL), and then dried with sodium sulfate. The solvent is evaporated in vacuo, and the residue is purified by flash chromatography with a 1:1 mixture of ethyl acetate and chloroform as eluant. The eluate is concentrated in vacuo, and the product could be further purified by recrystallization from the solution of ethyl acetate and DCM to give pure, colorless crystalline 5,5'-bis(diphenylphosphinoyl)-1,1',3,3'-tetramethyl-4,4'-bipyrimidine-2,2',6,6'-(1H,1'H,3H,3'H)-tetrone: $^1$H NMR (500 MHz) (CDCl$_3$) δ 3.32 (s, 6H), 3.41 (s, 6H), 6.94-6.98 (m, 4H), 7.15-7.18 (m, 2H), 7.45-7.57 (m, 10H), 8.03-8.07 (m, 4H); $^{13}$C-NMR (126 MHz) (CD$_2$Cl$_2$) δ 28.4, 34.0, 104.7 (d, J=113 Hz), 127.8 (d, J=13.9 Hz), 128.2 (d, J=12.6 Hz), 131.7 (d, J=81.3 Hz), 131.8, 131.8 (d, J=12.3 Hz), 132.6 (d, J=86.9

Hz), 132.4 (d, J=2.5 Hz), 133.7 (d, J=10.1 Hz), 153.9 (d, J=12.6 Hz), 161.5 (d, J=8.8 Hz); $^{31}$P-NMR (202 MHz) (CDCl$_3$) δ 29.1 (s).

EXAMPLE 4

Optical Resolution of 5,5'-Bis(diphenylphosphinoyl)-1,1',3,3'-tetramethyl-4,4'-bipyrimidine-2,2',6,6'-(1H,1'H,3H,3'H)-tetrone To a mixture of racemic 5,5'-bis(diphenylphosphinoyl)-1,1',3,3'-tetramethyl-4,4'-bipyrimidine-2,2',6,6'-(1H,1'H,3H,3'H)-tetrone from Example 3 (1.4 g, 2.1 mmol) and (−)-dibenzoyl-L-tartaric acid [(−)-DBTA)] (0.78 g, 2.1 mmol) is added 15 mL of ethyl acetate and 15 mL of chloroform. The mixture is heated to dissolve and is refluxed for 24 h. Then it is naturally cooled down to room temperature and is maintained for another 24 h at ambient temperature. Crystals of a 1:1 complex of (R)-5,5'-bis(diphenylphosphinoyl)-1,1',3,3'-tetramethyl-4,4'-bipyrimidine-2,2',6,6'-(1H,1'H,3H,3'H)-tetrone and (−)-DBTA are formed. The complex is collected by filtration, washed 3 times with chloroform and dried. (The mother liquor and the wash solution mainly contained the (S) enantiomer which could be resolved by (+)-DBTA). The complex is stirred with 20 mL 5% aqueous sodium hydroxide solution and 20 mL of chloroform until it is completely dissolved. The organic layer is separated, washed with water (3×20 mL), dried with anhydrous sodium sulfate and concentrated in vacuo to afford crude (R)-5,5'-bis(diphenylphosphinoyl)-1,1',3,3'-tetramethyl-4,4'-bipyrimidine-2,2',6,6'-(1H,1'H,3H,3'H)-tetrone. This procedure is repeated for another two times to afford pure (R)-5,5'-bis(diphenylphosphinoyl)-1,1',3,3'-tetramethyl-4,4'-bipyrimidine-2,2',6,6'-(1H,1'H,3H,3'H)-tetrone.

The (S) isomer can be resolved by the same procedure with (+)-DBTA.

EXAMPLE 5

(R)- or (S)-5,5'-Bis(diphenylphosphino)-1,1',3,3'-tetramethyl-4,4'-bipyrimidine-2,2',6,6'-(1H,1'H,3H,3'H)-tetrone; (R)- or (S)-PM-Phos

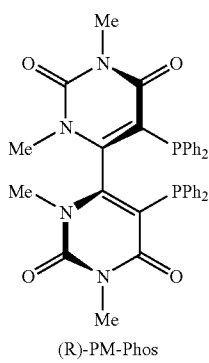

(R)-PM-Phos

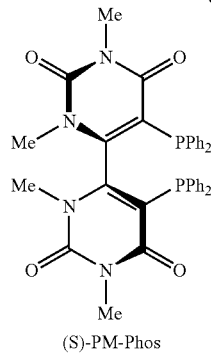

(S)-PM-Phos

A 50 mL glasslined autoclave equipped with a magnetic stirring bar is charged with 400 mg (0.60 mmol) of (R)- or (S)-5,5'-bis(diphenylphosphinoyl)-1,1',3,3'-tetramethyl-4,4'-bipyrimidine-2,2',6,6'-(1H,1'H,3H,3'H)-tetrone from Example 4, 1.2 mL (12 mmol) of trichlorosilane, 1.6 mL (12 mmol) of triethtylamine and 5 mL of toluene. The autoclave is closed and the mixture is heated with stirring in an oil bath at 120° C. to 140° C. for 1-3 days. After the completion of the reaction, the mixture is cooled down to ambient temperature and 30 mL of chloroform is added with stirring followed by the dropwise addition of 3 mL of 50% aqueous sodium hydroxide solution. The mixture is filtered through a short silica gel column with suction, and the column is washed by chloroform for 3 times. The combine filtrate is concentrated in vacuo to give a crude product, which is purified by recrystallization in 10 mL of chloroform to afford pure, colorless crystalline (R)- or (S)-5,5'-bis(diphenylphosphino)-1,1',3,3'-tetramethyl-4,4'-bipyrimidine-2,2',6,6'-(1H, 1'H,3H,3'H)-tetrone, (R)-PM-Phos: $^1$H NMR (500 MHz) (CDCl$_3$) δ 3.17 (s, 6H), 3.37 (s, 6H), 6.99-7.10 (m, 10H), 7.36-7.42 (m, 6H), 7.74-7.77 (m, 4H); $^{13}$C-NMR (126 MHz) (CD$_2$Cl$_2$) δ 28.7, 34.3, 127.6, 127.8 (d, J=3.8 Hz), 128.7 (d, J=8.8 Hz), 130.2, 131.1 (d, J=2.5 Hz), 131.2 (d, J=2.5 Hz), 134.3 (d, J=8.8 Hz), 135.2 (d, J=3.8 Hz), 135.8 (d, J=23.9 Hz), 151.6, 153.9 (d, J=3.8 Hz), 154.3 (d, J=5.0 Hz), 160.7; $^{31}$P-NMR (202 MHz) (CD$_2$Cl$_2$) δ −12.7 (s).

EXAMPLE 6

Preparation of a Palladium Catalyst Comprising (R)-PM-Phos and its Application in Catalytic Asymmetric Allylic Alkylation

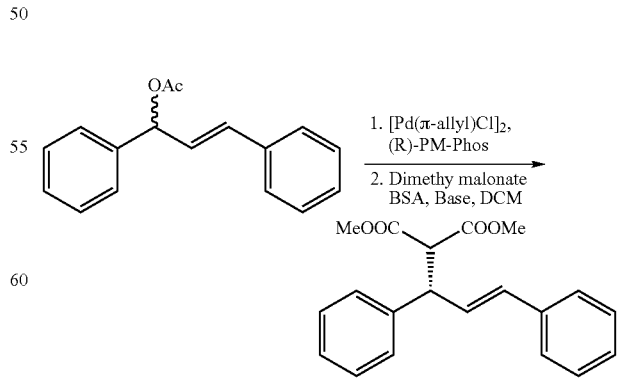

To a stirred solution of [Pd(π-allyl)Cl]$_2$ (0.18 mg, 5.0×10$^{-4}$ mmol) in 0.5 mL of DCM is added (R)-PM-Phos from Example 5 (0.71 mg, 1.1×10⁻³ mmol) under nitrogen atmosphere. After 1 h, racemic 1,3-diphenylallyl acetate (25 mg 0.10 mmol) in 0.5 mL of DCM is added and the solution is stirred for 0.5 h. N,O-bis(trimethylsilyl)acetamide (BSA, 0.074 mL, 0.30 mmol), dimethyl malonate (0.035 mL, 0.30 mmol) and NaOAc (0.4 mg, 0.005 mmol) are added and the solution is stirred at 25° C. The reaction is monitored by TLC. After 2 h, the solvent is evaporated in vacuo and column chromatography on silica gel (hexane:EtOAc—8:1) of the residue affords the product in the (S)-configuration in 85.2% ee (the enantiomeric excess is determined by HPLC: Daicel Chiracel AD column, 1.0 mL/min, hexane:i-PrOH—95:5).

EXAMPLE 7

Preparation of a Palladium Catalyst Comprising (R)-PM-Phos and its Application in Catalytic Asymmetric Allylic Amination

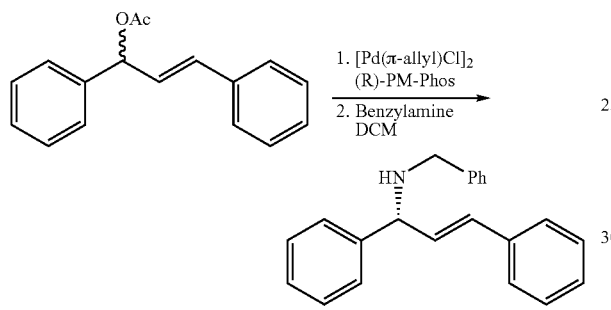

To a stirred solution of [Pd(π-allyl)Cl]₂ (0.37 mg, 1.0×10⁻³ mmol) in 0.5 mL of DCM is added (R)-PM-Phos from Example 5 (1.4 mg, 2.2×10⁻³ mmol) under nitrogen atmosphere. After 1 h, racemic 1,3-diphenylallyl acetate (25 mg 0.10 mmol) in 0.5 mL of DCM is added and the solution is stirred for 0.5 h. Benzylamine (0.026 mL, 0.24 mmol) was added and the solution is stirred at 25° C. The reaction was monitored by TLC. After 2 h, the solvent is evaporated in vacuo and column chromatography on silica gel (hexane: EtOAc—5:1) of the residue affords the product in the (R)-configuration in 81.1% ee (the enantiomeric excess is determined by HPLC: Daicel Chiracel OJ column, 0.6 mL/min, hexane:i-PrOH—90:10).

What is claimed is:

1. A compound of the formula

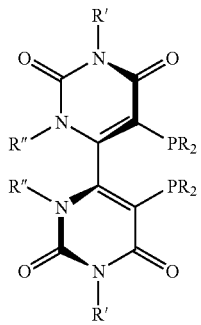

(I)

wherein
R is optionally substituted alkyl, cycloalkyl, aryl or heteroaryl;

R' and R" are independently optionally substituted alkyl, cycloalkyl, aryl or heteroaryl;

or an enantiomer thereof; or an enantiomeric mixture thereof.

2. A compound according to claim 1, wherein
R is monocyclic aryl;
R' and R" are independently lower alkyl;
or an enantiomer thereof; or an enantiomeric mixture thereof.

3. A compound according to claim 2, wherein
R is phenyl;
R' and R" are methyl;
or an enantiomer thereof; or an enantiomeric mixture thereof.

4. A compound according to claim 1, which is selected from the group consisting of:
(R)-5,5'-bis(disubstitutedphosphino)-1,1',3,3'-tetraalkyl-4,4'-bipyrimidine-2,2',6,6'-(1H,1'H,3H,3'H)-tetrone; and
(S)-5,5'-bis(disubstitutedphosphino-1,1',3,3'-tetraalkyl-4,4'-bipyrimidine-2,2',6,6'-(1H,1'H,3H,3'H)-tetrone.

5. A method for preparing a compound of the formula

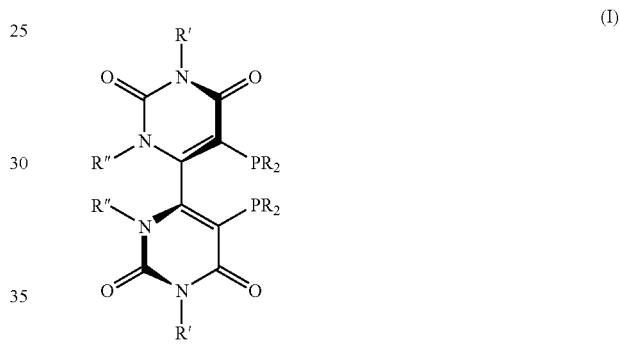

(I)

wherein R is optionally substituted alkyl, cycloalkyl, aryl or heteroaryl; R' and R" are independently optionally substituted alkyl, cycloalkyl, aryl or heteroaryl; or an enantiomer thereof; or an enantiomeric mixture thereof, which method comprises reducing a compound of the formula

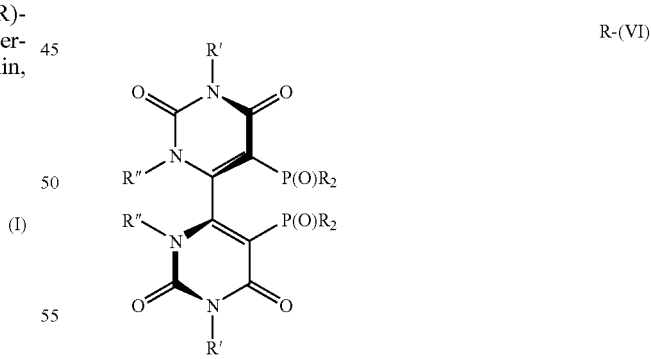

R-(VI)

wherein R is optionally substituted alkyl, cycloalkyl, aryl or heteroaryl; R' and R" are independently optionally substituted alkyl, cycloalkyl, aryl or heteroaryl; or respectively, an enantiomer thereof; or an enantiomeric mixture thereof; with a reducing agent in the presence of an organic base and an aromatic hydrocarbon solvent to afford a compound of formula (I) wherein the reducing agent is trichlorosilane the organic base is triethylamine, the aromatic hydrocarbon solvent is toluene and the reduction reaction is carried out in an autoclave.

6. A method for preparing a compound of the formula

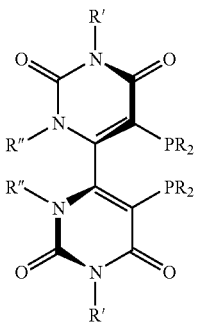

(I)

wherein R is optionally substituted alkyl, cycloalkyl, aryl or heteroaryl; R' and R" are independently optionally substituted alkyl, cycloalkyl, aryl or heteroaryl; or an enantiomer thereof; or an enantiomeric mixture thereof; which method comprises reducing a compound of the formula

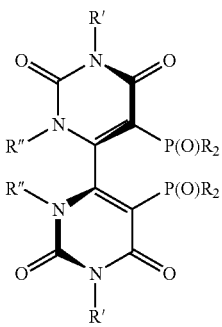

R-(VI)

wherein R is optionally substituted alkyl, cycloalkyl, aryl or heteroaryl; R' and R" are independently optionally substituted alkyl, cycloalkyl, aryl or heteroaryl; or respectively, an enantiomer thereof; or an enantiomeric mixture thereof; with a reducing agent in the presence of an organic base and an aromatic hydrocarbon solvent to afford a compound of formula (I), wherein the reducing agent is trichlorosilane, the organic base is triethylamine, the aromatic hydrocarbon solvent is toluene, wherein a compound of formula R-(VI); or an enantiomer thereof; or an enantiomeric mixture thereof; is prepared by a process comprising:

(a) converting by coupling reaction a compound of the formula

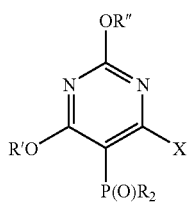

(V)

wherein R, R' and R" have meanings as defined in said claim and X represents halogen; to a compound of the formula

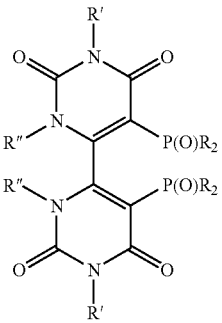

(VI)

wherein R, R' and R" have meanings as defined for formula (V); in the presence of copper powder, an inert solvent and an inorganic salt, wherein the inert solvent is selected from the group consisting of tetrahydrofuran, acetone, N,N-dimethylformamide and dimethylsulfoxide and the inorganic salt is selected from the group consisting of sodium carbonate, potassium carbonate, sodium oxalate, and a mixture thereof; and (b) resolving a resulting compound of formula (VI) into its optical antipodes of the formula

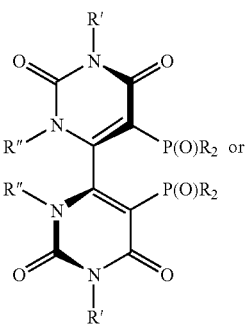

R-(VI) or

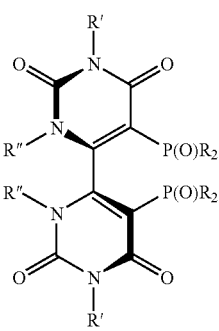

S-(VI)

wherein R, R' and R" have meanings as defined for formula (VI); or an enantiomeric mixture thereof.

* * * * *